United States Patent
Shah et al.

(10) Patent No.: US 9,393,336 B2
(45) Date of Patent: Jul. 19, 2016

(54) INSERT FOR DISPENSING A COMPRESSED GAS PRODUCT, SYSTEM WITH SUCH AN INSERT, AND METHOD OF DISPENSING A COMPRESSED GAS PRODUCT

(75) Inventors: Bhaveshkumar Shah, Kenosha, WI (US); Nitin Sharma, Kenosha, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 840 days.

(21) Appl. No.: 13/428,945

(22) Filed: Mar. 23, 2012

(65) Prior Publication Data

US 2013/0008982 A1    Jan. 10, 2013

Related U.S. Application Data

(60) Provisional application No. 61/457,925, filed on Jul. 8, 2011.

(51) Int. Cl.
| | |
|---|---|
| *B05B 17/04* | (2006.01) |
| *A61L 9/14* | (2006.01) |
| *B05B 7/10* | (2006.01) |
| *B05B 1/34* | (2006.01) |
| *A01M 1/20* | (2006.01) |
| *B65D 83/20* | (2006.01) |
| *B65D 83/48* | (2006.01) |

(52) U.S. Cl.
CPC ............... *A61L 9/14* (2013.01); *A01M 1/2038* (2013.01); *B05B 1/3426* (2013.01); *B05B 1/3436* (2013.01); *B05B 1/3478* (2013.01); *B05B 7/10* (2013.01); *B65D 83/206* (2013.01); *B65D 83/48* (2013.01); *Y10T 137/0318* (2015.04); *Y10T 137/2087* (2015.04)

(58) Field of Classification Search
CPC ..................................................... B05B 1/3436
USPC .......... 239/1, 11, 337, 463–497; 700/14, 283; 222/1

See application file for complete search history.

(56) References Cited

U.S. PATENT DOCUMENTS

| | | |
|---|---|---|
| 3,207,386 A | 9/1965 | Presant et al. |
| 3,436,772 A | 4/1969 | Stebbins |
| 3,600,325 A | 8/1971 | Kaufman et al. |
| 3,854,636 A | 12/1974 | Conway et al. |
| 4,139,128 A | 2/1979 | Ewald |
| 4,248,380 A | 2/1981 | Lee et al. |
| 4,536,323 A | 8/1985 | Stopper |
| 4,605,165 A | 8/1986 | Van Loveren et al. |
| 4,740,366 A | 4/1988 | Winston et al. |

(Continued)

FOREIGN PATENT DOCUMENTS

| | | |
|---|---|---|
| CN | 2645674 Y | 10/2004 |
| DE | 272422 A1 | 10/1989 |

(Continued)

*Primary Examiner* — Len Tran
*Assistant Examiner* — Alexander Valvis

(57) ABSTRACT

An insert, a system, and a method are provided for dispensing a compressed gas product. The insert includes a swirl chamber, inlet ports to the swirl chamber, and an outlet orifice. The insert has specifically configured parameters relating to the diameter of the swirl chamber, the diameter of the outlet orifice, the length of the outlet orifice, and the depth of the swirl chamber. The insert, system, and method can provide a dispensed compressed gas product with a remarkably constant flow rate and with a remarkably constant particle size.

13 Claims, 3 Drawing Sheets

(56) References Cited

U.S. PATENT DOCUMENTS

| | | | |
|---|---|---|---|
| 4,752,020 | A | 6/1988 | Grueter et al. |
| 4,805,839 | A | 2/1989 | Malek |
| 4,851,212 | A | 7/1989 | Winston et al. |
| 4,940,170 | A | 7/1990 | Popp-Ginsbach |
| 4,940,171 | A | 7/1990 | Gilroy |
| 4,988,464 | A * | 1/1991 | Riley ............................... 264/12 |
| 5,143,288 | A | 9/1992 | Kohler et al. |
| 5,164,740 | A | 11/1992 | Ivri |
| 5,232,127 | A | 8/1993 | Trotta et al. |
| 5,263,616 | A | 11/1993 | Abplanalp |
| 5,271,533 | A | 12/1993 | Joulia |
| 5,297,566 | A | 3/1994 | Firstenberg et al. |
| 5,305,930 | A | 4/1994 | De Laforcade |
| 5,370,317 | A | 12/1994 | Weston |
| 5,400,975 | A * | 3/1995 | Inculet et al. ............... 239/690.1 |
| 5,817,293 | A | 10/1998 | Akehurst et al. |
| 5,862,960 | A | 1/1999 | Miller et al. |
| 5,918,780 | A | 7/1999 | Tanaka |
| 5,918,817 | A | 7/1999 | Kanno et al. |
| 5,938,117 | A | 8/1999 | Ivri |
| 6,077,318 | A | 6/2000 | Trinh et al. |
| 6,161,735 | A | 12/2000 | Uchiyama et al. |
| 6,199,766 | B1 | 3/2001 | Fox et al. |
| 6,279,834 | B1 | 8/2001 | Fox et al. |
| 6,338,442 | B1 | 1/2002 | De Laforcade |
| 6,440,912 | B2 | 8/2002 | McGee et al. |
| 6,482,357 | B1 | 11/2002 | Fox et al. |
| 6,540,153 | B1 | 4/2003 | Ivri |
| 6,592,813 | B1 | 7/2003 | Fox et al. |
| 6,629,646 | B1 | 10/2003 | Ivri |
| 6,729,559 | B2 | 5/2004 | Zanma et al. |
| 6,767,507 | B1 | 7/2004 | Woo et al. |
| 6,770,247 | B1 | 8/2004 | Romack et al. |
| 6,789,702 | B2 | 9/2004 | O'Connor et al. |
| 6,824,079 | B2 | 11/2004 | Kendrick et al. |
| 6,921,020 | B2 | 7/2005 | Ivri |
| 6,987,099 | B2 | 1/2006 | Trinh et al. |
| 7,014,127 | B2 | 3/2006 | Valpey, III et al. |
| 7,083,112 | B2 | 8/2006 | Ivri |
| 7,128,067 | B2 * | 10/2006 | Byron ............... A61M 11/041 128/200.14 |
| 7,182,941 | B2 | 2/2007 | Trinh et al. |
| 7,237,697 | B2 | 7/2007 | Dunne |
| 7,364,055 | B2 | 4/2008 | Yquel et al. |
| 7,909,264 | B2 | 3/2011 | Dunne et al. |
| 8,927,474 | B2 | 1/2015 | Shah |
| 2001/0011687 | A1 | 8/2001 | Benoist |
| 2002/0002123 | A1 | 1/2002 | McGee et al. |
| 2002/0059941 | A1 | 5/2002 | Garnier et al. |
| 2003/0029931 | A1 | 2/2003 | Zanma et al. |
| 2003/0089739 | A1 | 5/2003 | O'Connor et al. |
| 2003/0150885 | A1 | 8/2003 | Dunne |
| 2003/0199402 | A1 | 10/2003 | Triplett et al. |
| 2004/0000598 | A1 | 1/2004 | Ivri |
| 2004/0028785 | A1 | 2/2004 | Langourieux et al. |
| 2004/0071646 | A1 | 4/2004 | Pataut et al. |
| 2004/0223871 | A1 | 11/2004 | Woo et al. |
| 2004/0223943 | A1 | 11/2004 | Woo et al. |
| 2005/0023368 | A1 * | 2/2005 | Valpey et al. .................... 239/1 |
| 2005/0098588 | A1 | 5/2005 | Dunne |
| 2005/0124512 | A1 | 6/2005 | Woo et al. |
| 2005/0150971 | A1 * | 7/2005 | Zhou ................. 239/1 |
| 2005/0279851 | A1 | 12/2005 | Ivri |
| 2006/0263236 | A1 | 11/2006 | Woo et al. |
| 2007/0122373 | A1 | 5/2007 | Woo et al. |
| 2009/0020621 | A1 | 1/2009 | Clark et al. |
| 2009/0084870 | A1 * | 4/2009 | Smith ................. B65D 83/753 239/303 |
| 2010/0276507 | A1 * | 11/2010 | Labegorre et al. ............. 239/11 |
| 2012/0018539 | A1 | 1/2012 | Horiuchi et al. |
| 2013/0008540 | A1 | 1/2013 | Shah et al. |

FOREIGN PATENT DOCUMENTS

| | | |
|---|---|---|
| EP | 0 510 352 A2 | 10/1992 |
| EP | 0 639 149 A1 | 2/1995 |
| HK | 1032547 A1 | 4/2004 |
| JP | 03-282139 A | 12/1991 |
| JP | 6174264 A | 6/1994 |
| JP | 10-503952 T | 4/1998 |
| JP | 2001-072152 A | 3/2001 |
| JP | 2001-233390 A | 8/2001 |
| JP | 2002-048016 A | 2/2002 |
| JP | 2002-309242 A | 10/2002 |
| JP | 2002-369873 A | 12/2002 |
| JP | 2003-012422 A | 1/2003 |
| JP | 2004-049600 A | 2/2004 |
| MX | PA03007943 A | 5/2004 |
| WO | 00/01429 A2 | 1/2000 |
| WO | 00/40479 A1 | 7/2000 |
| WO | 02/13771 A2 | 2/2002 |
| WO | 02/051364 A2 | 7/2002 |

* cited by examiner

INSERT FOR DISPENSING A COMPRESSED GAS PRODUCT, SYSTEM WITH SUCH AN INSERT, AND METHOD OF DISPENSING A COMPRESSED GAS PRODUCT

The application claims priority to U.S. Provisional Application No. 61/457,925, filed Jul. 8, 2011.

BACKGROUND

1. Field of the Invention

Our invention relates to an insert for dispensing a compressed gas product, a system that includes such an insert, and a method of dispensing a compressed gas product. More generally, our invention relates to apparatuses, systems, and methods for dispensing compressed gas products with a relatively constant flow rate and with a relatively constant particle size.

2. Related Art

In general, aerosol dispensers provide low cost, easy to use methods of dispensing products, typically, as an airborne mist. Thus, aerosol dispensers have been commonly used to dispense personal, household, industrial, and medical products. The airborne mist provided by an aerosol dispenser itself may provide a desired effect, as is the case with air freshening fragrances. Alternatively, the mist may be used to form a thin coating on surfaces, such as with furniture polishes.

Typically, aerosol dispensing systems include a container that holds a product with liquid and gas parts. Examples of liquid compositions included in aerosol systems are air and fabric fresheners, soaps, insecticides, paints, deodorants, disinfectants, and the like. The gas included with the liquid product acts as a propellant to discharge the liquid product from the container. The propellant pressurizes the container holding the liquid composition, and provides a force to expel the liquid composition from the container when a user actuates the aerosol dispenser by pressing an actuator button or trigger.

There are two main types of propellants used in aerosol systems: (1) liquefied gas propellants, such as hydrocarbon and hydrofluorocarbon (HFC) propellants, and (2) compressed gas propellants, such as carbon dioxide and nitrogen. In the past, chlorofluorocarbon propellants (CFCs) were used as propellants in aerosol systems. The use of CFCs, however, has essentially been phased out due to the potentially harmful effects of CFCs on the environment.

In an aerosol system that uses a liquefied petroleum gas-type propellant (LPG), the container is loaded with liquid composition and LPG propellant to a pressure approximately equal to the vapor pressure of the LPG. After being filled, the container has a certain amount of space that is not occupied by liquid. This space is referred to as the headspace. Since the container is pressurized to approximately the vapor pressure of the LPG propellant, some of the LPG is dissolved or emulsified in the liquid product. The remainder of the LPG remains in the vapor phase and fills the headspace. As the product is dispensed, the pressure in the container remains approximately constant because liquid LPG moves from the liquid to the vapor in the headspace, thereby replenishing discharged LPG propellant vapor.

In contrast, compressed gas propellants in aerosol systems largely remain in the vapor phase. That is, only a relatively small portion of a compressed gas propellant is contained in the liquid composition. Hence, a "compressed gas product" includes a liquid composition and a compressed gas propellant. As a result, the pressure within a compressed gas aerosol dispenser assembly decreases as the product is dispensed. While this aspect of using compressed gas propellants is, in some ways, disadvantageous, the use of compressed gas propellants has gained favor as compressed gas propellants do not usually contain volatile organic compounds (VOCs). On the other hand, LPGs are considered to be VOCs, thereby making their use subject to various regulations.

From a consumer satisfaction standpoint, an important aspect of an aerosol system is that the system provides a consistent fragrance experience provided by a consistent flow rate and a consistent particle size. A consistent flow rate and a consistent particle size ensures that a relatively consistent effect is achieved as the product is dispensed from the container. For example, in the case of air freshening products, the fragrance experience is a function of the amount of fragrance in the air, which in turn is related to both the flow rate and particle size of product dispensed by the related system. Thus, it is important that the flow rate and particle size of product that is dispensed when the container is relatively full be as close as possible to the flow rate and particle size of product that is dispensed when the container is relatively empty so that the user can achieve the same levels of air freshening with equal lengths of application, regardless of the amount of product remaining in the container.

Ideally, in an aerosol system configured to dispense an air freshener, the system dispenses a product with a flow rate and a particle size such that a sufficient amount of fragrance experience is achieved soon after the dispensing, but also such that there is longevity in the fragrance experience. The higher the flow rate of product from the system, the more fragrance that will be available with a given length of application. Too high of flow rate, however, may lead to an overwhelming fragrance experience. With respect to particle size, larger particles provide a smaller total surface area for evaporation of the fragrance as compared to an equivalent volume of smaller particles. The smaller surface area for evaporation of fragrance in larger particles provides for less of an initial fragrance experience compared to an equivalent volume of smaller particles. However, the smaller surface area for evaporation of fragrance in larger particles provides for a longer fragrance experience compared to an equivalent volume of smaller particles, i.e., the fragrance evaporates more slowly from the larger particles. Still other factors are taken into account when considering the particle size for an air freshener. Smaller particles may be more easily carried away with air flow, which also reduces the longevity of the fragrance experience. On the other hand, there is a greater tendency for larger particles to fall out of the air and onto surfaces. Such fall out behavior of larger particles is often undesirable because of the resulting accumulation on a surface.

Ideally, an aerosol system is configured to provide a flow rate and particle size that balances these considerations. That is, the aerosol system provides a flow rate and particle size such that a sufficient amount of fragrance is available quickly after dispensing the product, with the product particle sizes providing longevity to the fragrance experience, but not so large to present substantial fall out. With compressed gas propellants, however, there is a tendency for the spray rate to decrease as the product is dispensed from a container. Further, there is a tendency for the particle size to increase as the product is dispensed from the container. In prior art dispensing systems, the flow rate may decrease by more than 40% as the product in the container is used up. In the same prior art systems, the particle size may increase by more than 50% as the product in the container is used up. Accordingly, the desired effects of the dispensed product achieved by having a consistent flow rate and a consistent particle size are not found in prior art compressed gas aerosol systems. Further, even if the initial flow rate and initial particle size can provide an air freshener with a good fragrance experience, the changes in the flow rate and particle size may degrade the fragrance experience.

SUMMARY OF THE INVENTION

According to one aspect of the invention, an insert is provided for use with an assembly to dispense a compressed gas product from a container. The insert comprises a swirl chamber having a diameter Ds and a depth Ls, at least one inlet port opening to the swirl chamber, and an outlet orifice having a diameter do and a length lo. The insert is configured such that Ds/do is about 3.0 to about 3.5, lo/do is about 0.4 to about 0.6, and Ls/Ds is about 0.3 to about 1.0.

Another aspect of the invention is a method of dispensing a compressed gas product from a container and a dispenser assembly that includes an insert with a swirl chamber. The method comprises providing a product in the container such that the pressure inside the container is less than about 157 psi. The product is dispensed from the container through the insert such that the flow rate of product out of the insert when the container is about 13% full of product is at least about 65% that of the initial flow rate of product when the container is 100% full of product.

Yet another aspect of the invention is a method of dispensing a compressed gas product from a container that includes an insert with a swirl chamber. The method comprises providing a product in the container such that the pressure inside the container is less than about 157 psi, and dispensing the product from the container through the insert such that the particle size increases by less than about 40% as the amount of product in the container drops to 13% of the initial amount of product in the container.

Another aspect of the invention is related to a method of minimizing a change in flow rate of a compressed gas product and minimizing an increase in particle size of the compressed gas product dispensed from a container through a dispenser assembly that includes an insert. The insert has (i) a swirl chamber with a diameter Ds and a length Ls, (ii) at least one inlet port opening to the swirl chamber, the at least one inlet port having a cross-sectional area Ap, and (iii) an outlet orifice having a diameter do and a length lo. The method comprises adjusting the ratio Ds/do to be in the range of about 3.0 to about 3.5, adjusting the ratio lo/do to be in the range of about 0.4 to about 0.6, adjusting the ratio Ls/Ds to be in the range of about 0.3 to about 1.0, and adjusting the ratio Ap/(Ds·do) to in the range of about 0.3 to about 0.9.

According to a further aspect of the invention, a system is provided for dispensing a compressed gas product. The system comprises a container for containing a volume of compressed gas product, and a compressed gas product inside the container, with the compressed gas product including a compressed gas component and a liquid component. The compressed gas product dispensed from the container has a flow rate of (i) at least about 2.0 g/s during an initial ten second dispensing period from the container, and (ii) at least about 1.3 g/s during a ten second dispensing period when the container has about 13% of the initial amount of compressed gas product remaining in the container.

According to another aspect of the invention, a system is provided for dispensing a compressed gas product. The system comprises a container for containing a volume of compressed gas product, with the compressed gas product including a compressed gas component and a liquid component. The compressed gas product dispensed from the container has a flow rate of (i) at least about 2.0 g/s during an initial ten second dispensing period from the container, (ii) at least about 1.7 g/s during a ten second dispensing period when the container has about 66% of the initial amount of compressed product remaining, (iii) at least about 1.4 g/s during a ten second dispensing period when the container has about 33% of the initial amount of compressed product remaining, and (iv) at least about 1.3 g/s during a ten second dispensing period when the container has about 13% of the initial amount of the compressed gas product remaining.

A different aspect of the invention is directed to a system for dispensing a compressed gas product. The system comprises a container, and a compressed gas product provided inside the container, with the compressed gas product including a compressed gas component and a liquid component. The system is configured to dispense the compressed gas product with a flow rate of such that a flow rate of compressed gas product when the system is about 13% full of product is at least about 65% that of an initial flow rate of product when the system is 100% full of product. The system is also configured to dispense the compressed gas product such that the particle size increases by less than about 40% as the amount of product in the container drops to 13% of the initial amount of product in the container.

In other aspects of the invention, a method is provided for minimizing a change in flow rate of a compressed gas product and minimizing an increase in particle size of the compressed gas product dispensed from a container through an insert provided to a dispenser assembly associated with the container. The insert has (i) a swirl chamber with a diameter Ds and a length Ls, (ii) at least one inlet port opening to the swirl chamber, the at least one inlet port having a cross-sectional area Ap, and (iii) an outlet orifice having a diameter do and a length lo. The method comprises adjusting the ratio Ds/do, adjusting the ratio lo/do, adjusting the ratio Ls/Ds, and adjusting the ratio Ap/(Ds·do). A spray rate during an initial sixty second dispensing of the compressed gas product through the insert is at least about 1.7 g/s.

Another aspect of the invention is directed to a method of maintaining a spray rate of compressed gas product. The method comprises providing the compressed gas product inside a container such that the pressure inside the container is less than about 157 psi, and dispensing the compressed gas product from the container. The compressed gas product has a flow rate of at least about 1.7 g/s during an initial sixty second dispensing from the container, and the spray rate decreases by less than about 0.7 g/s as the compressed gas product is discharged from a full container to a point when the container has about 13% of the compressed gas product remaining.

DETAILED DESCRIPTION OF THE INVENTION

Our invention is related to an insert for dispensing a compressed gas product, a system that includes such an insert, and a method of dispensing a compressed gas product. As will be described below, the insert can be used with an aerosol dispenser assembly to dispense a compressed gas product from a container in a manner that maintains a relatively constant flow rate and a relatively constant particle size. Similarly, a method according to the invention provides steps for dispensing a compressed gas product with a relatively constant flow rate and a relatively constant particle size.

Figure 1:
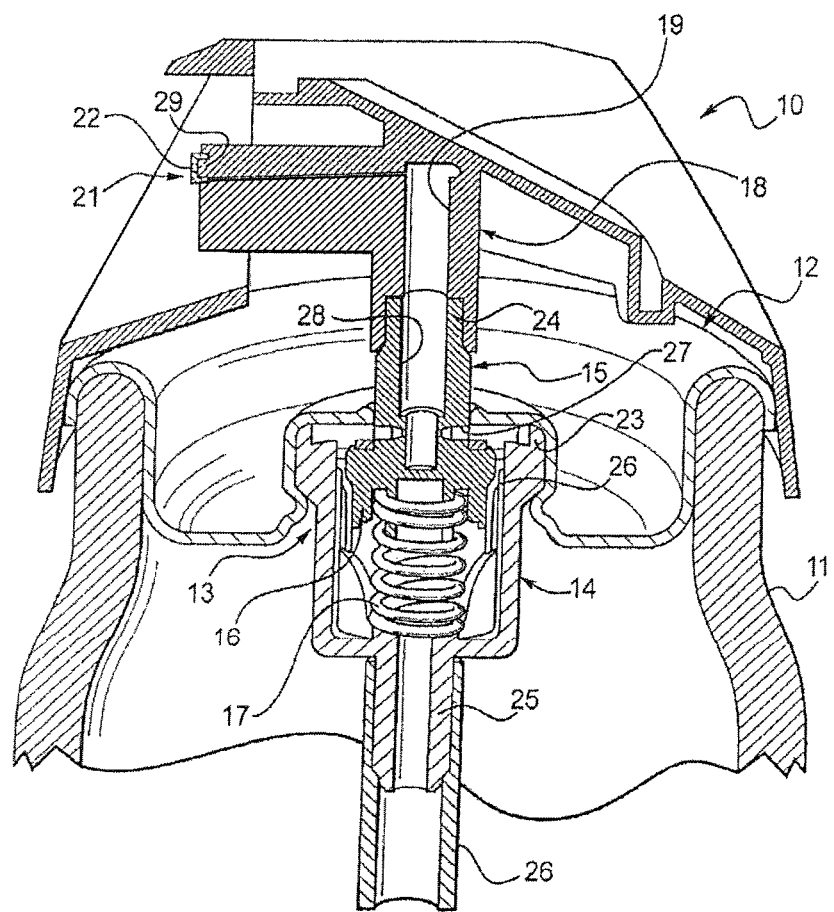
FIG. 1 is a cross-sectional view of an aerosol dispenser having an insert according to the invention.

FIG. 1 depicts an aerosol dispenser assembly 10 that includes an insert 21 according to the invention. The aerosol dispenser assembly 10 includes a container 11 covered by a mounting cup 12. A mounting gasket (not shown) may be disposed between an upper rim of the container 11 and the underside of the mounting cup 12. A valve assembly 13 is used to selectively release the contents from the container 11 to the atmosphere. The valve assembly 13 comprises a valve body 14 and a valve stem 15. The valve stem 15 includes a lower end 16 that extends through a return spring 17. An actuator body 18 is mounted on top of the valve stem 15 and defines a primary passageway 19. The actuator body 18 is also connected to the nozzle insert 21 that defines an exit orifice shown generally at 22. The insert 21 will be discussed in greater detail below.

An upper rim 23 of the valve body 14 is affixed to the underside of the mounting cup 12 by a friction fit and the valve stem 15 extends through the mounting cup 12. The actuator body 18 is frictionally fitted onto the upwardly extending portion 24 of the valve stem 15. The lower end 25 of the valve body 14 is connected to a dip tube 26. Gaskets may or may not be provided between the valve body 14 and the mounting cup 12, and between the valve stem 15 and the mounting cup 12, depending upon the materials used for each component. Suitable materials that will permit a gasket-less construction will be apparent to those skilled in the art. Similarly, gaskets or seals are typically not required between the actuator body 18 and the upper portion 24 of the valve stem 15. While the dispenser assembly 10 of FIG. 1 employs a vertical action-type actuator body or cap 18, other actuator cap designs may be used, such as an actuator button with an integral over cap, a trigger actuated assembly, a tilt action-type actuator cap, or other designs.

In operation, when the actuator body 18 is depressed, the valve stem 15 moves downward, thereby allowing pressurized liquid product to be propelled upward through the dip tube 26 and the lower portion 25 of the valve body 14 by the propellant. From the valve body 14, the product is propelled past the lower end 16 of the valve stem 14 through the channel 26 and through the stem orifice(s) 27, out the passageway 28 of the valve stem and into the primary passageway 19 of the actuator body 18. In some embodiments, two valve stem orifices 27 are employed, as is shown in FIG. 1, although a single valve stem orifice 27 or more than two valve stem orifices 27 may be used. Multiple valve stem orifices 27 may provide greater flow and superior mixing of the compressed gas product.

It should be noted that while specific features and a configuration for a system for providing a compressed gas product are exemplified in the dispenser assembly 10, our invention is not limited to such features and configuration. Indeed, as will be appreciated by those skilled in the art, a wide variety of dispenser assemblies could be used with the inventive insert, systems, and methods described herein.

FIGS. 2-5 show an example embodiment of an insert 21 according to the invention. The insert 21 includes a sidewall 32 that defines a substantially circular shape, and an endwall 29 that includes an outlet orifice 22. It should be noted, however, the shape of the sidewall could be varied such that the insert 21 includes, for example, a plurality of sidewalls defining a rectangular shape or any other polygonal shape. Of course, the corresponding slot in the actuator body of the dispenser assembly that receives the insert 21 will be shaped to correspond to the shape of the sidewall 29.

The insert 21 includes a plurality of inlet ports 30 that lead to a swirl chamber 31. The swirl chamber 31 is in fluid communication with the outlet orifice 22. Thus, the insert 21 provides a fluid pathway from the inlet ports 30 to the swirl chamber 31, and then out of the insert 21 through the outlet orifice 22. Thus, a compressed gas product contained in a system including a container and dispenser assembly, such as those described above, can be dispensed through the fluid pathway in the insert 21.

The configuration of the swirl chamber 31 and the tangentially positioned inlet ports 30 creates a swirling motion to the liquid in the chamber 31. As a result, a core of air extends from the rear of the swirl chamber 31 to the outlet orifice 22. Thus, the product dispensed from the outlet orifice 22 is released as an annular sheet, which spreads radially outward to form a hollow conical spray. It should be noted that although four inlet ports 30 are shown in the depicted embodiment, the number of inlet ports 30 can be any number, including only a single inlet port. The number of inlet ports 30 will depend on factors such as, for example, the size of the corresponding system, the desired shape of the system, etc.

Figure 2:
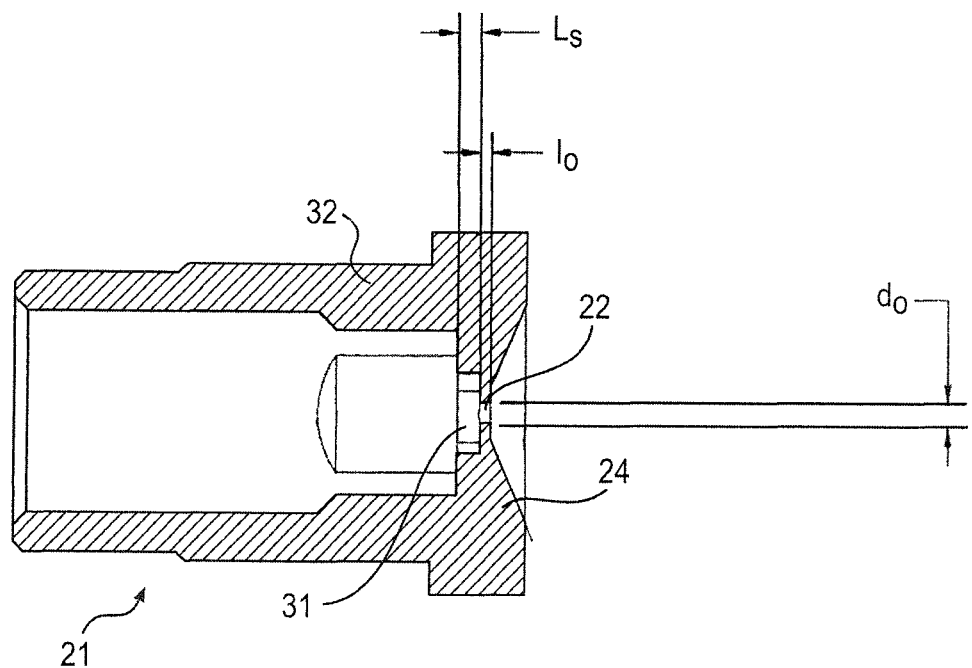
FIG. 2 is a cross-sectional view of an insert according to the invention.
Figure 3:
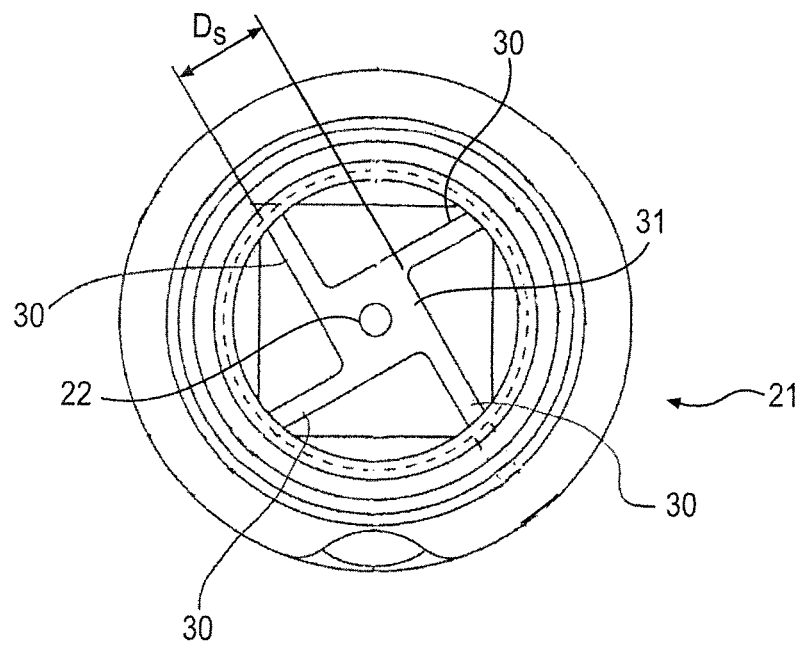
FIG. 3 is a cross-sectional view of the swirl chamber of the insert shown in FIG. 2.
Figure 4:
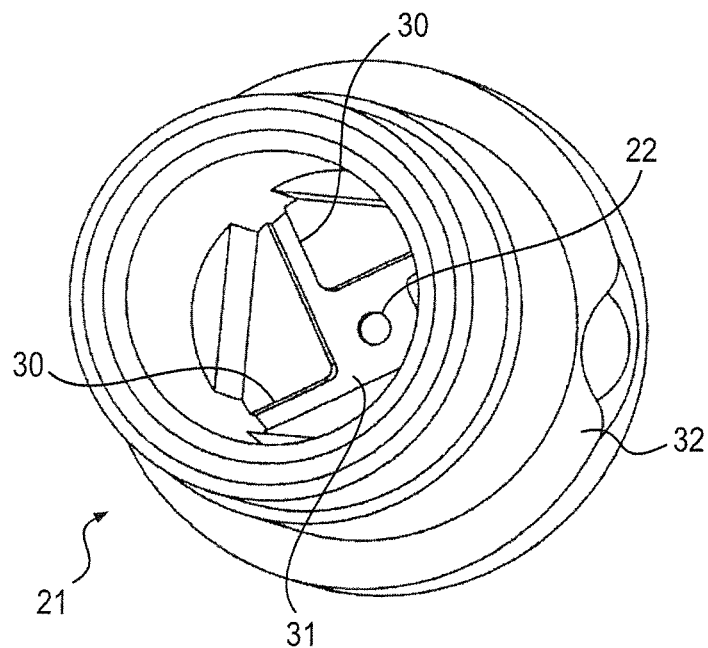
FIG. 4 is a rear elevation view of the insert shown in FIG. 2.
Figure 5:
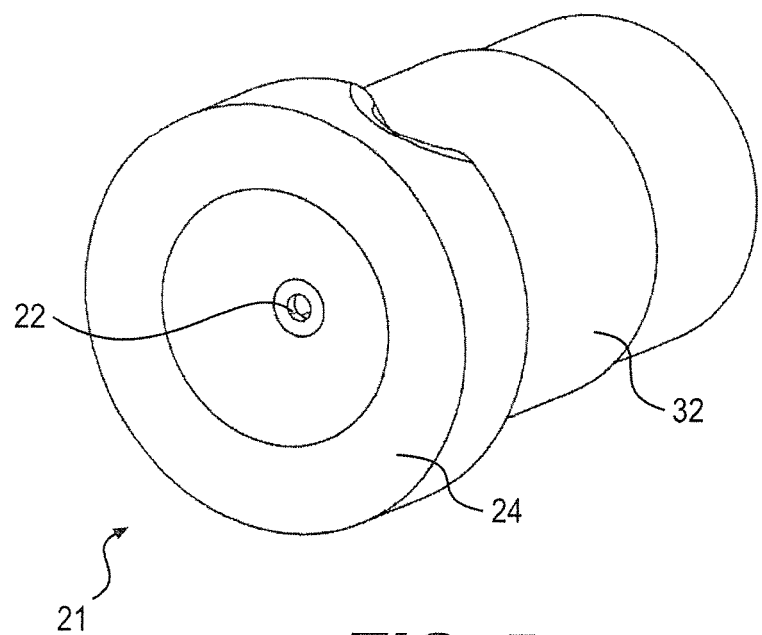
FIG. 5 is a front elevation view of the insert shown in FIG. 2.

Certain parameters of the insert 21 are shown in FIGS. 2 and 3. One such parameter is the "diameter" $D_s$ of the swirl chamber 31. As is apparent from FIGS. 3-4, the swirl chamber 31 has a substantially square shape. In view of the substantially square shape, the diameter $D_s$ represents the maximum diameter of a circle that can be contained in the swirl chamber 31. In alterative embodiments, however, the swirl chamber 31 can have a circular shape, wherein the diameter $D_s$ is the actual diameter of the chamber.

Other parameters of the swirl chamber 31 and outlet orifice 22 are shown in FIG. 2. One such parameter is the depth of the swirl chamber $L_s$. In this case, the depth $L_s$ is the same size as the depth of the inlet ports 30 provided to the swirl chamber 31. In other embodiments, however, the depth of the swirl chamber 31 may be different from the depths of the inlet ports 30. Parameters of the outlet orifice 22 include a diameter $d_o$, and a length $l_o$ that the outlet orifice extends from the swirl chamber 31 to the final outlet of insert 21.

The inlet ports 30 leading to the swirl chamber 31 are substantially rectangular in shape, and therefore have a length and depth (or width). As such, the inlet ports 30 provide a total cross-sectional area $A_p$ opening to the swirl chamber 31. As noted above, that the number of inlet ports 25 provided to the swirl chamber 31 can be varied. Along these lines, the shape and angle of the ports 30 with respect to the swirl chamber 31 can also be varied. It should be noted, however, that regardless of aspects such as the number, shape, and positioning of the inlet ports 30, differently configured inlet ports still can provide the equivalent cross-sectional areas $A_p$.

Prior art nozzle inserts have included swirl chambers, inlet ports, and exit orifices. And attempts have been made in the prior art to adjust some of the parameters of these structures in order to achieve various effects in dispensing compressed gas products. For example, U.S. Patent Application Pub. No. 2009/0020621, the disclosure of which is incorporated by reference in its entirety, discloses a design methodology for an actuator body and a swirl nozzle (insert) so as to maintain a small particle size using a compressed gas VOC-free propellant for an air freshener product. What we have surprisingly found is that certain ratios of parameters, including the diameter of the swirl chamber $D_s$, the diameter of the outlet orifice do, the length of the outlet orifice lo, the depth of the swirl chamber Ls, and the total cross-sectional areas of the inlet ports Ap, can lead to remarkably consistent flow rates and remarkably consistent particle sizes when dispensing compressed gas products using the insert. In particular, when the insert is configured such that Ds/do is 3.0 to 3.5, lo/do is 0.4 to 0.6, Ls/Ds is 0.3 to 1.0, and Ap/(Ds·do) is 0.3 to 0.9, surprisingly low amount of decrease in the flow rate occurs as a compressed gas product is dispensed from a compressed gas system that uses the insert. These same ratios also provide surprisingly low rates of increase in particle size as a compressed gas product is dispensed from the container. The effect of these ratios will be demonstrated in the tests set forth below.

Without being limited by any theory, it is believed that if the ratios of Ds/do, lo/do, Ls/Ds, and Ap/(Ds·do) are outside the ranges described above, the swirling and particle breakup of the product that occurs in the swirl chamber changes more significantly as the product is dispensed from the container. As discussed above, unlike LPG in LPG systems, the amount of compressed gas propellant in a system is reduced as the product is dispensed. This aspect of a compressed gas system may contribute to the decrease in flow rate and the increase in particle size as the compressed gas product is dispensed. On the other hand, having the above-described ratios of parameters in the identified ranges may act to negate some of the effects of the reduced amount of compressed gas on the flow rate and particle size.

As will be appreciated by those skilled in the art, a wide variety of compressed gas products can be used in systems according to the invention. As non-limiting examples, such compressed gas products can include air fresheners, combination air and fabric fresheners, refreshers, deodorizers, sanitizers, disinfectants, soaps, insecticides, insect repellants, fertilizers, herbicides, fungicides, algaecides, pesticides, rodenticides, paints, deodorants, deodorants, body sprays, hair sprays, topical sprays, cleaners, polishes, and shoe or footwear spray products. Examples of specific compressed gas product formulations that can be used with apparatuses, systems, and methods according to the invention are set forth in U.S. patent application Ser. No. 13/422,096, the disclosure of which is incorporated by reference in its entirety. Along these lines, one of ordinary skill in the art will appreciate that properties of such compressed gas products, including viscosity, density, and surface tension, can easily be adjusted to achieve desired effects. In example embodiments, the density of the compressed gas product is about 1.00 g/cm$^3$, the surface tension is about 30 mN/m, and the viscosity is about 1.0-1.6 cP.

The particular type of compressed gas that is used as the propellant in systems according to the invention can be selected based on convenience, cost, properties of the corresponding container, properties of the liquid product formulation, etc. Examples of known compressed gases that can be used in systems according to the invention include air, argon, nitrogen, nitrous oxide, inert gases, and carbon dioxide. Along with the particular type of compressed gas, the amount of headspace provided by the compressed gas can be adjusted or tailored as desired. As compressed gases do not significantly dissolve in the liquid portion of a compressed gas product, the amount of headspace is primarily a function of the amount of compressed gas used in the container. In example embodiments of systems according to the invention, a headspace of 30 to 40% is used. However, in alternative embodiments the headspace could be lower than 30% or higher than 40%.

The container for use in systems of the invention may be a metallic container, such as a steel or aluminum canister, or combinations thereof. Alternatively, the container could be manufactured using any plastic or resin. Example of such plastics or resins include polyethylene terepthalate (PET), preferably clear PET, polycarbonate, polyacrylate, polyethylene naphthalate (PEN), a sandwhich layer plastic such as ethylene vinyl alcohol copolymer (EVOH) and PET, a copolyester such as is sold under the trademark TRITON™ by Eastman Chemical Company of Kingsport, Tenn., or impact-modified acrylonitrile-methyl acrylate copolymers such as are sold under the trademark BAREX® by Ineos Olefins & Polymers of League City, Tex. Of course, one of ordinary skill in the art will recognize that there are other materials that could also be used to manufacture the canister.

The container can also be adopted for the particular compressed gas formulation, as is described in the aforementioned U.S. patent application Ser. No. 13/422,096, or other alternative compressed gas formulations. As will be appreciated by those skilled in the art, containers used to provide compressed gas products are required by law to be made in accordance with Department of Transportation (DOT) and Interstate Commerce Commission (ICC) regulations. These regulations mandate certain dimensional, material, manufacture, wall thickness, and testing requirements for a container to be charged to a given pressure. For example, a 2P rated container can be used if the internal pressure is from 140 to 160 psig at 130° F., and a 2Q rated container can be used if the internal pressure is from 161 to 180 psig at 130° F. In general, the containers used in conjunction with the present invention can be adjusted to meet these regulations, and as such, be used to provide a compressed gas product at any given pressure in the container. In particular embodiments, however, systems of the invention are specifically designed as 2Q and 2P rated containers. Example embodiments of the invention include containers initially charged with up to 157 psig at 70° F. of compressed gas product.

Insert Parameter and Container Pressure Testing

In order to determine the effect of the above-described parameters of an insert on the flow rate and particle size of a dispensed compressed gas product, a series of tests was conducted with different inserts. The parameters of the inserts varied, and the parameters are listed in Table 1 below. In Table 1, the same abbreviations for the insert parameters are used as are described above. Specifically, the diameter of the outlet orifice is labeled do, the diameter of the swirl chamber is labeled Ds, the length of the outlet orifice is labeled lo, the depth of the swirl chamber is labeled Ls, and the total cross-sectional area of the inlet ports to the swirl chamber is labeled Ap. The values of all of these parameters are given in inches, except for the cross-sectional area Ap, which is given in square inches. Table 1 further indicates the number of inlet ports "n" leading to the swirl chamber of each insert.

The flow rates indicated in Table 1 were determined by discharging systems including the inserts for sixty seconds. The flow rate was measured using a stopwatch and a scale made by Mettler-Toledo of Columbus, Ohio. All of the other parameters of the system, such as the configuration of the dispenser assembly and container, the size of the containers, the initial pressure in the containers, etc., were the same for all of the inserts. Additionally, all of the tests were conducted at ambient temperature (about 70° F.).

TABLE 1

| Insert | do | Ds | Ds/do | lo | lo/do | n | Ls | Ls/Ds | Ap | $\frac{Ap}{(Ds \cdot do)}$ | Flow Rate (g/s) |
|---|---|---|---|---|---|---|---|---|---|---|---|
| 1 | 0.014 | 0.046 | 3.30 | 0.007 | 0.50 | 4 | 0.010 | 0.22 | 0.0004 | 0.6184 | 1.40 |
| 2 | 0.014 | 0.046 | 3.30 | 0.011 | 0.79 | 4 | 0.008 | 0.17 | 0.0003 | 0.3958 | 1.15 |
| 3 | 0.013 | 0.046 | 3.54 | 0.011 | 0.85 | 4 | 0.010 | 0.22 | 0.0004 | 0.6689 | 1.11 |
| 4 | 0.015 | 0.046 | 3.07 | 0.007 | 0.47 | 4 | 0.011 | 0.24 | 0.0005 | 0.7014 | 1.50 |
| 5 | 0.015 | 0.046 | 3.07 | 0.007 | 0.47 | 4 | 0.015 | 0.33 | 0.0006 | 0.8696 | 1.72 |
| 6 | 0.013 | 0.041 | 3.15 | 0.013 | 1.00 | 5 | 0.008 | 0.20 | 0.0007 | 1.2758 | 1.56 |
| 7 | 0.015 | 0.031 | 2.07 | 0.011 | 0.73 | 5 | 0.015 | 0.48 | 0.0009 | 1.9355 | 1.79 |

As demonstrated by the data in Table 1, the parameters do, Ds, lo, Ls, and Ap function together synergistically to affect the flow rate dispensed through an insert. That is, while one of the parameters, such as the diameter of the outlet orifice, might be directly related to the flow rate, the actual flow rate is a result of the combination of all the parameters.

More importantly, we found from tests such as those shown in Table 1 that the above-described specific ratios of Ds/do, lo/do, Ls/Ds, and Ap/(Ds·do) lead to surprisingly consistent flow rates and particle sizes. Further tests demonstrating our findings with respect to the ratio of parameters are described below.

Tests were also conducted to correlate the pressure of the container having an insert according to the invention with the amount of product remaining in the container. The results of these tests are shown in Table 2.

TABLE 2

| % of Full Container | Target Fill Weight (g) | Pressure Measurements (psig) | | | |
|---|---|---|---|---|---|
| | | Sample 1 | Sample 2 | Sample 3 | Average |
| 100 | 227 | 135 | 136 | 136 | 135.6 ± 0.5 |
| 90 | 204 | 116 | 116 | 117 | 116.3 ± 0.5 |
| 80 | 182 | 100 | 101 | 100 | 100.3 ± 0.5 |
| 66 | 150 | 86 | 87 | 87 | 86.6 ± 0.5 |
| 50 | 113 | 72 | 72 | 72 | 72.0 ± 0.0 |

TABLE 2-continued

| % of Full Container | Target Fill Weight (g) | Pressure Measurements (psig) | | | |
|---|---|---|---|---|---|
| | | Sample 1 | Sample 2 | Sample 3 | Average |
| 33 | 75 | 61 | 62 | 61 | 61.3 ± 0.5 |
| 13 | 30 | 51 | 52 | 51 | 51.3 ± 0.53 |
| 0 | 0 | 42 | 36 | 40 | 39.3 ± 3.0 |

As can be seen from the data in Table 2, the pressure in the container of the system ranged from about 135 psig when the container was initially filled with the compressed gas product, to about 40 psig when all of the compressed gas product had been dispensed from the container. These pressures can be directly correlated to the amount of product remaining in the container in the tests involving Insert A described below.

Insert Parameter Comparison Testing

An insert A according to the invention was compared in the tests discussed below to the inserts B and C, which were provided on compressed gas product dispensing systems that are sold in retail stores.

The insert A according to the invention was provided on a system that included a dispenser assembly and associated container, as generally described above. The container initially included 227 grams (about 8 ounces) of an air freshening product, and nitrogen was used as the gas propellant. The container was initially pressurized to about 135-138 psi with the compressed gas product, and had 36% headspace. The parameters of insert A are shown in Table 3 below.

The insert B was part of a product available in retail stores. The system with insert B included a container having 226 grams of an air freshening product. Insert C was also part of a product available in retail stores. The system with insert C included a container having 275 grounds of an air freshening product. The specific parameters for inserts B and C are shown in Table 3 below.

The same abbreviations and units of measure for the insert parameters are used in Table 3 as are used in Table 1 above.

TABLE 3

| Insert | do | Ds | Ds/do | lo | lo/do | n | Ls | Ls/Ds | Ap | $\frac{Ap}{(Ds \cdot do)}$ |
|---|---|---|---|---|---|---|---|---|---|---|
| A | 0.015 | 0.046 | 3.07 | 0.007 | 0.47 | 4 | 0.015 | 0.32 | 0.00060 | 0.8696 |
| B | 0.013 | 0.053 | 4.07 | 0.010 | 0.77 | 4 | 0.010 | 0.19 | 0.00060 | 0.8708 |
| C | 0.014 | 0.038 | 2.71 | 0.015 | 1.07 | 3 | 0.010 | 0.26 | 0.00042 | 0.7894 |

It should be noted that some of the individual parameters of Insert A shown in Table 3 are not significantly different from the parameters for Inserts B and C. For example, the diameter do of the outlet orifice for Insert A is very close to the diameters do for Inserts B and C, and the diameter of the swirl chamber Ds of Insert A falls between the diameters Ds for Inserts B and C. Some of the ratios of parameters for Insert A, however, such as Ds/do, lo/do, and Ls/Ds are significantly different than the ratios for Inserts B and C. As discussed above, it is believed that configuring an insert with these ratios leads to a surprisingly consistent flow rate and surprisingly consistent particle size as the compressed gas product is dispensed, and tests demonstrated such consistency in the dispensed product are discussed below.

Sixty Second Spray Comparisons

The flow rates dispensed from compressed gas systems using inserts A, B, and C were compared. In each case, three fully charged systems having the inserts were provided, and each of the systems was discharged for sixty seconds. The flow rate was determined using a stopwatch and a scale made by Mettler-Toledo of Columbus, Ohio. All of the tests were conducted at ambient temperature (about 70° F.). The results of the flow rate tests are shown in Table 4.

TABLE 4

| Sample | Flow Rate (g/sec.) | | |
|---|---|---|---|
| Number | Insert A | Insert B | Insert C |
| 1 | 1.85 | 1.48 | 1.18 |
| 2 | 1.85 | 1.45 | 1.35 |
| 3 | 1.84 | 1.43 | 1.39 |
| Average | 1.85 ± 0.005 | 1.45 ± 0.02 | 1.30 ± 0.011 |

The results shown in Table 4 indicate that Insert A had a higher flow rate than did Inserts B and C.

The average particle size dispensed from Inserts A, B, and C was determined in a sixty second dispensing test. In this test, the samples from three fully charged systems with Insert A were dispensed and the particle size was determined using a particle analyzer made by Malvern Instruments of Malvern, Worcestershire, UK. A mass median diameter (MMD) of particles in the samples was thereby obtained, with the MMD representing a particle diameter that is larger than 50% of the sampled volume. All of the tests were conducted at ambient temperature (about 70° F.). The result of the test is shown in Table 5.

TABLE 5

| Sample | Particle Size (μm) | | |
|---|---|---|---|
| Number | Insert A | Insert B | Insert C |
| 1 | 63.01 | 74.18 | 66.01 |
| 2 | 67.08 | 75.52 | 68.95 |
| 3 | 65.59 | 76.01 | 68.82 |
| Average | 65.23 ± 2.05 | 75.23 ± 0.9 | 67.86 ± 1.6 |

As can be seen from the results shown in Table 5, Insert A provided during the sixty second dispensing test an average particle size of about 65 μm, while Inserts B and C provided average particle sizes of about 75 μm and 68 μm, respectively.

As discussed above, in the case of air fresheners a goal is to dispense a product with a flow rate and a particle size such that a sufficient amount of fragrance experience is achieved soon after the dispensing, while at the same time dispensing the product in a manner that provides for longevity of the fragrance experience. In embodiments of the present invention, the combination of flow rate and particle size that were found in the sixty second dispensing tests using Insert A are conducive to both a favorable initial fragrance experience and a sustained fragrance experience.

Ten Second Spray Comparisons

The flow rates and particle sizes in ten second sprays from systems that included the Inserts A, B, and C were compared. In each case, three systems having the inserts were provided, and the systems were discharged for ten seconds. The flow rates and average particle sizes (MMD) were determined according to the methods described above. The tests were then repeated when the containers had 66%, 33%, and 13% of the initial amount of product (by mass) remaining in the containers. All of the tests were conducted at ambient temperature (about 70° F.).

The results of the tests are shown in Tables 6-9 below. Table 6 show the results of the 10 second spray from 100% full containers. Tables 7, 8, and 9 show the results from 66%, 33%, and 13% full (by mass) containers, respectively.

TABLE 6

100% Full Containers

| | Insert A | | Insert B | | Insert C | |
|---|---|---|---|---|---|---|
| Sample Number | Spray Rate (g/s) | Particle Size (μm) | Spray Rate (g/s) | Particle Size (μm) | Spray Rate (g/s) | Particle Size (μm) |
| 1 | 2.03 | 67.32 | 1.73 | 70.14 | 1.58 | 61.69 |
| 2 | 2.04 | 65.69 | 1.68 | 70.22 | 1.65 | 60.43 |
| 3 | 2.04 | 61.61 | 1.74 | 70.61 | 1.51 | 59.36 |
| Average | 2.036 ± 0.01 | 64.96 ± 3.0 | 1.72 ± 0.03 | 70.32 ± 0.25 | 1.58 ± 0.07 | 60.49 ± 1.16 |

TABLE 7

66% Full Containers

| | Insert A | | Insert B | | Insert C | |
|---|---|---|---|---|---|---|
| Sample Number | Spray Rate (g/s) | Particle Size (μm) | Spray Rate (g/s) | Particle Size (μm) | Spray Rate (g/s) | Particle Size (μm) |
| 1 | 1.69 | 70.68 | 1.37 | 77.84 | 1.22 | 70.64 |
| 2 | 1.68 | 69.25 | 1.34 | 79.04 | 1.32 | 67.11 |
| 3 | 1.66 | 75.85 | 1.35 | 82.18 | 1.16 | 73.56 |
| Average | 1.67 ± 0.01 | 71.93 ± 3.47 | 1.35 ± 0.01 | 79.68 ± 2.24 | 1.23 ± 0.08 | 70.44 ± 3.23 |

TABLE 8

33% Full Containers

| | Insert A | | Insert B | | Insert C | |
|---|---|---|---|---|---|---|
| Sample Number | Spray Rate (g/s) | Particle Size (μm) | Spray Rate (g/s) | Particle Size (μm) | Spray Rate (g/s) | Particle Size (μm) |
| 1 | 1.42 | 75.23 | 1.17 | 93.31 | 1.00 | 81.89 |
| 2 | 1.44 | 78.38 | 1.13 | 95.57 | 1.11 | 79.71 |
| 3 | 1.42 | 75.67 | 1.15 | 98.91 | 0.94 | 82.45 |
| Average | 1.43 ± 0.01 | 76.43 ± 1.70 | 1.15 ± 0.02 | 95.93 ± 2.82 | 1.02 ± 0.08 | 81.35 ± 1.45 |

TABLE 9

13% Full Containers

| | Insert A | | Insert B | | Insert C | |
|---|---|---|---|---|---|---|
| Sample Number | Spray Rate (g/s) | Particle Size (μm) | Spray Rate (g/s) | Particle Size (μm) | Spray Rate (g/s) | Particle Size (μm) |
| 1 | 1.33 | 87.47 | 1.05 | 109.4 | 0.89 | 91.12 |
| 2 | 1.35 | 80.13 | 1.06 | 117.5 | 0.96 | 89.46 |
| 3 | 1.31 | 87.47 | 1.01 | 107.2 | 0.82 | 90.42 |
| Average | 1.33 ± 0.02 | 85.02 ± 4.24 | 1.04 ± 0.03 | 111.3 ± 5.25 | 0.89 ± 0.07 | 90.33 ± 0.83 |

As is evident from Tables 6-9, the flow rate of product dispensed using Insert A remained much more constant than the flow rates of the products dispensed using Inserts B and C. The flow rate of Insert A, which was about 2.0 g/s for the initial 10 second dispensing, dropped by 18% to about 1.7 g/s when the amount of product remaining was 66% the original amount of product. When 33% of the original amount of product remained, the flow rate had dropped 30% to about 1.4 g/s, and decreased by about 35% to about 1.3 g/s when 13% of the original amount of product remained in the container. In other words, the flow rate when the container was 13% full of product was still about 65% that of the flow rate when the container was full. On the other hand, the flow rates using Inserts B and C had decreased by about 40% and about 44%, respectively, when 13% of the initial amount of product remained in the containers of the systems. Moreover, at every measured step, i.e., 66%, 33%, and 13% product remaining, the flow rate using Insert A decreased by a lower percentage than the flow rates decreased using Inserts B and C. Thus, Insert A provided a significantly more consistent flow rate as the product was discharged from the system.

As is also evident from Tables 6-9, the particle size dispensed with Insert A remained much more constant than the particle size dispensed with Inserts B and C. The particle size using Insert A, which was about 65 μm for the initial 10 second dispensing, increased by 11% to about 72 μm when the amount of product remaining was 66% the original amount. When 33% of the original amount of product remained, the particle size had increased by about 18% to about 76 μm, and increased by about 31% to about 85 μm when 13% of the original amount of product remained in the container. On the other hand, the particle size using Inserts B and C had increased by about 58% and about 49%, respectively, when 13% of the initial amount of product remained in the containers of the systems. Moreover, at every measured step, i.e., 66%, 33%, and 13% product remaining, the particle size using Insert A increased by a lower percentage than the particle sizes increased using Inserts B and C. Thus, Insert A provided a significantly more consistent particle size as the product was discharged from the system.

As discussed above, important aspects of a system of providing an aerosol product are consistent flow rate of product and consistent particle size. While the flow rate dispensed using Insert A decreased and the particle size increased, the relative amount of change in these aspects of product performance was significantly less than what occurred in the commercially-available systems that included Inserts B and C. Based on a comparison of the parameters of the Inserts A, B, and C shown in Table 3, it is apparent that the above-identified ratios involving the diameter of the swirl chamber Ds, the diameter of the outlet orifice do, the length of the outlet orifice lo, and the depth of the swirl chamber Ls, are responsible for the surprisingly stable flow rates and stable particle sizes found when using Insert A. Indeed, these results are all the more surprising when considering that, as noted above, some of these parameters for Insert A were, in and of themselves, nearly the same as the parameters found in Inserts B and C.

As discussed above, factors such as temperature, pressure in the container, and properties of the product formulation, such as density and surface tension, might influence the performance of a compressed gas product, including the flow rate and particle size of the dispensed product. The above results clearly demonstrate, however, that at ambient temperature and over the pressure ranges tested, i.e., from about 150 psig to about 45 psig, a relatively consistent flow rate and relatively consistent average particle size can be obtained by configuring the dispensing insert with the combination of parameters described above. Moreover, as one of ordinary skill in the art will readily appreciate, while the actually measured flow rate and particle size that are dispensed with a given insert might be changed by a change in the temperature, pressure, product formulation, etc., the above-described combinations of parameters of the insert that are used to achieve the relatively constant flow rate and relatively constant particle size will remain the same.

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

INDUSTRIAL APPLICABILITY

The inventive apparatuses, systems, and methods described herein can be used to dispense a wide variety of commercial products, such as air fresheners, soaps, insecticides, paints, deodorants, disinfectants. As such, inventive apparatuses, systems, and methods described herein are applicable in a wide variety of industries.

We claim:

1. A method of dispensing a product from a container that includes a swirl chamber insert, the method comprising:

dispensing the product from the container through the swirl chamber insert, the dispensed product being in the form of an aerosol that includes (i) particles as a mist and (ii) a compressed gas propellant, and a mass mean diameter of the particles of the dispensed product increasing by less than about 40% as an amount of product in the container drops to 13% of an initial amount of product in the container, and wherein pressure inside the container with the initial amount of product is less than about 157 psi.

2. A method according to claim 1, wherein a flow rate of the dispensed product during an initial sixty second dispensing period from the container is at least about 1.7 g/sec.

3. A method according to claim 2, wherein the mass mean diameter of particles of the dispensed product during the sixty second dispensing period is about 65 μm.

4. A method according to claim 1, wherein a flow rate of the dispensed product when the container contains 13% of the initial amount of product is about 1.3 g/s.

5. A method according to claim 4, wherein the mass mean diameter of particles of the dispensed product when the container contains 13% of the initial amount of product is about 85 μm.

6. A method according to claim 1, wherein the pressure inside the container before dispensing any of the initial amount of product is about 135 psig.

7. A method according to claim 1, wherein the product includes an air freshening compound.

8. A method of dispensing an air freshening product from a container that includes a swirl chamber insert, the method comprising:

dispensing the air freshening product from the container through the swirl chamber insert, the dispensed air freshening product being in the form of an aerosol that includes (i) particles as a mist and (ii) a compressed gas propellant, a density of the dispensed air freshening product is about 1.00 g/cm$^3$, and a mass mean diameter of the particles of the dispensed air freshening product increasing by less than about 40% as an amount of air freshening product in the container drops to 13% of an initial amount of air freshening product in the container, and wherein pressure inside the container with the initial amount of air freshening product is less than about 157 psi.

9. A method according to claim 8, wherein the pressure inside the container before dispensing any of the initial amount of air freshening product is about 135 psig.

10. A method according to claim 8, wherein a flow rate of the dispensed air freshening product during an initial sixty second dispensing period from the container is at least about 1.7 g/sec.

11. A method according to claim 10, wherein the mass mean diameter of particles of the dispensed air freshening product during the sixty second dispensing period is about 65 µm.

12. A method according to claim 8, wherein a flow rate of the dispensed air freshening product when the container contains 13% of the initial amount of air freshening product is about 1.3 g/s.

13. A method according to claim 12, wherein the mass mean diameter of particles of the dispensed air freshening product when the container contains 13% of the initial amount of air freshening product is about 85 µm.

\* \* \* \* \*